United States Patent
Ochiai et al.

(10) Patent No.: US 8,652,841 B2
(45) Date of Patent: Feb. 18, 2014

(54) CULTURE METHODS OF BONE MARROW STROMAL CELLS AND MESENCHYMAL STEM CELLS, AND MANUFACTURE METHOD OF GRAFT CELLS FOR CENTRAL NERVE SYSTEM DISEASES THERAPY

(75) Inventors: Toshimasa Ochiai, Hyogo (JP); Louis Yuge, Hiroshima (JP); Yumi Kawahara, Hiroshima (JP)

(73) Assignees: Mitsubishi Heavy Industries, Ltd., Tokyo (JP); Louis Yuge, Hiroshima (JP); Yumi Kawahara, Hiroshima (JP)

( * ) Notice: Subject to any disclaimer, the term of this patent is extended or adjusted under 35 U.S.C. 154(b) by 0 days.

(21) Appl. No.: 13/264,219

(22) PCT Filed: Apr. 12, 2010

(86) PCT No.: PCT/JP2010/056503
§ 371 (c)(1),
(2), (4) Date: Dec. 27, 2011

(87) PCT Pub. No.: WO2010/119828
PCT Pub. Date: Oct. 21, 2010

(65) Prior Publication Data
US 2012/0115224 A1    May 10, 2012

(30) Foreign Application Priority Data
Apr. 13, 2009 (JP) ................. 2009-097509

(51) Int. Cl.
*A61K 38/00* (2006.01)

(52) U.S. Cl.
USPC ........... 435/325; 435/363; 435/366; 435/375; 435/377

(58) Field of Classification Search
None
See application file for complete search history.

(56) References Cited

FOREIGN PATENT DOCUMENTS

| EP | 1577380 A1 | 9/2005 |
|---|---|---|
| JP | 2007-68447 A | 3/2007 |
| WO | 2004/061092 A1 | 7/2004 |

OTHER PUBLICATIONS

Lu, Dunyue et al.; "Adult bone marrow stromal cells administered intravenously to rats after traumatic brain injury migrate into brain and improve neurological outcome"; NeuroReport, vol. 12, No. 3, Mar. 5, 2001, pp. 559-563.

Bang Oh Young, MD, PhD, et al; "Autologous Mesenchymal Stem Cell Transplantation in Stroke Patients"; American Neurological Association 2005, Annals of Neurology, vol. 57, No. 6, Jun. 2005, pp. 874-882.

International Search Report of PCT/JP2010/056503, mailing date Jun. 8, 2010.

Okazaki, Takahito et al.; "Intravenous administration of bone marrow stromal cells increases survivin and Bcl-2 protein expression and improves sensorimotor function following ischemia in rats"; Neuroscience Letters 430, (2008), pp. 109-114.

Honma, T. et al.; "Intravenous infusion of immortalized human mesenchymal stem cells protects against injury in a cerebral ischemia model in adult rat"; Experimental Neurology, 199, (2006), pp. 56-66.

(Continued)

*Primary Examiner* — Blaine Lankford
*Assistant Examiner* — Thomas J Visone
(74) *Attorney, Agent, or Firm* — Westerman, Hattori, Daniels & Adrian, LLP

(57) ABSTRACT

In a culture method of the present invention, by culturing bone marrow stromal cells or mesenchymal stem cells under a pseudo micro-gravity environment generated by multi-axis rotation, bone marrow stromal cells or mesenchymal stem cells having an average cell size smaller than that before the culture are obtained. The bone marrow stromal cells or mesenchymal stem cells thus cultured are suitable as graft cells for a central nerve diseases therapy.

1 Claim, 14 Drawing Sheets

(56) References Cited

OTHER PUBLICATIONS

Chen, Jieli et al.; "Therapeutic Benefit of Intravenous Administration of Bone Marrow Stromal Cells After Cerebral Ischemia in Rats"; Stroke, Journal of the American Heart Association, 2001, vol. 32, pp. 1005-1011.

Yuge, Louis et al.; "Effectiveness of Bone Marrow Stromal Cell Cultured under Microgravity in Neurogenesis"; Space Utiliz. Res., 2009, vol. 25, pp. 104-105.

Yuge, Louis et al.; "Human mesenchymal stem cell proliferation and differentiation using a 3D-clinostat culture"; Gravitational and Space Biol., 2005, vol. 19, No. 1, p. 36 ( Abstract [80]).

Yuge Louis et al.; "Microgravity Potentiates Stem Cell Proliferation While Sustaining the Capability of Differentiation"; Stem Cells Dev., 2006, vol. 15, pp. 921-929.

Yuge Louis et al., "Simulated microgravity facilitates human mesenchymal stem cell proliferation and chondrocyte differentiation after transplantation"; Gravitational and Space Biol., 2004, vol. 18, No. 1, p. 60 (Abstract [12]).

Wang Yi et al.; "Stem Cell Transplantation: A Promising Therapy for Parkinson's Disease"; J. Neuroimmune Pharmacol., 2007, vol. 2, pp. 243-250.

Chen, Jieli Md et al.; "Intracerebral transplantation of bone marrow with BDNF after MCAo in rat", Neuropharmacology 39 (2000), Jan. 7, 2000, pp. 711-716.

Extended European Search Report dated Feb. 11, 2013, issued in corresponding European Patent Application No. 10764412.2.

Zayzafoon, M. et al., "Modeled Microgravity Inhibits Osteogenic Differentiation of Human Mesenchymal Stem Cells and Increases Adipogenesis", Endocrinology, vol. 145, No. 5, p. 2421-2432, Jan. 1, 2004; cited in Extended European Search Report dated Feb. 11, 2013.

Meyers, V. E. et al., "RhoA and Cytoskeletal Disruption Mediate Reduced Osteoblastogenesis and Enhanced Adipogenesis of Human Mesenchymal Stem Cells in Modeled Microgravity", Journal of Bone and Mineral Research, vol. 20, No. 10, p. 1858-1866, Oct. 1, 2005; cited in Extended European Search Report dated Feb. 11, 2013.

Fig. 2

| Target Gene (product size) | primer sequence (sense and antisense) | PCR condition |
|---|---|---|
| Oct-4 (430-bp) | 5'-CCG TGA AGT TGG AGA AGG TG-3'<br>5'-TGA TTG GCG ATG TGA GTG AT-3' | 34 cycles of 30 sec at 95°C, 30 sec at 60°C and 60 sec at 68°C |
| NF-H (202-bp) | 5'-AGC CCA AGG ACT CTA CAG CA-3'<br>5'-CTT TGG CTT TTC CGT CTC TG-3' | 34 cycles of 30 sec at 95°C, 30 sec at 60°C and 30 sec at 68°C |
| β-actin (450-bp) | 5'-GAG AGG GAA ATG GTG CGT GA-3'<br>5'-ACA TCT GCT GGA AGG TGG AC-3' | 34 cycles of 30 sec at 95°C, 45 sec at 58°C and 60 sec at 68°C |

| Exp. Group | Media* | GFP(%) | Diameter(μm) | % diameter |
|---|---|---|---|---|
| 1G | GM | 1.2 | 22.7 | 100[1] |
|  | ND | 4.2 | 23.5 | 100[2] |
| CL | GM | 7.3 | 19.9 | 87.7[1] |
|  | ND | 11.3 | 16.4 | 69.8[2] |

*GM: GROWTH MEDIA,
ND: NERVE DIFFERENTIATION INDUCING CULTURE MEDIA,
[1] RATIO OF CL-GM TO 1G-GM,
[2] RATIO OF CL-ND TO 1G-ND

| Exp. Group | Media* | PKH26 (%) | Cell Area ($\mu m^2$/cell) | % Cell Area |
|---|---|---|---|---|
| 1G | GM | 0.18 | 5495 | 100[1)] |
| CL | GM | 5.13 | 3141 | 56.8[1)] |

*GM:GROWTH MEDIA, [1)]RATIO OF CL-GM TO 1G-GM

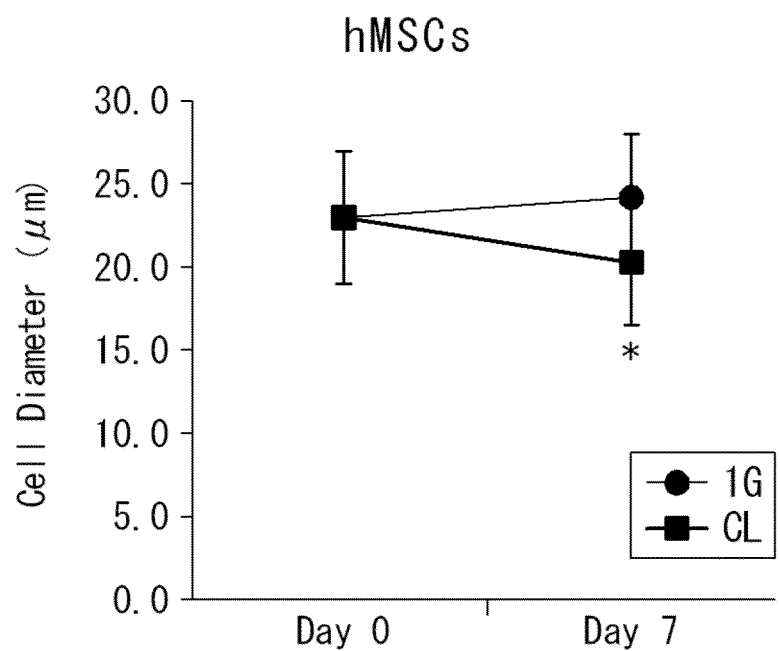

CULTURE METHODS OF BONE MARROW STROMAL CELLS AND MESENCHYMAL STEM CELLS, AND MANUFACTURE METHOD OF GRAFT CELLS FOR CENTRAL NERVE SYSTEM DISEASES THERAPY

TECHNICAL FIELD

The present invention relates to a culture method of bone marrow stromal cells, a culture method of mesenchymal stem cells, and a manufacture method of graft cells for a central nerve system diseases therapy.

BACKGROUND ART

Although the medical treatment of central nerve system diseases has been conventionally considered as difficult due to the impossibility of nerve regeneration, the regeneration medicine is recently attracting expectations as a new therapy. Conventionally, a method of transplanting embryonic stem cells or neural stem cells obtained from an embryo brain into the brain has been investigated as the regeneration medicine; however, this method faces immunological rejections, supply limitation of cells, and ethical problems.

As one of therapies for solving such problems, transplantation of bone marrow stromal cells (BMSCs) or mesenchymal stem cells (MSCs) obtained by isolation of bone marrow stromal cells has been proposed. For example, it was reported by Chen et al. in 2000 that a cell therapy of BMSCs into the brain was effective to rat cerebral infarction models (non-patent literature 1), and from then on, use of BMSCs has been recognized as one candidate of cell therapies of central nerve system diseases. BMSCs are easy to be obtained and have a low risk of immunological rejections due to the adaptability to autotransplantation, while causing less ethical problems.

Furthermore, intravenous transplantation of BMSCs has been investigated. Intravenous cell transplantation, which can be achieved by drip infusion as is the case with medicine infusion, is considered as non-filtrating and safer. Curative effects achieved by intravenous cell transplantation have been reported, for example, in non-patent literatures 2 to 6 described below and considered as near to practical application. Bang et el. reported that a clinical test involving intravenous autotransplantation of BMSCs for patients of middle cerebral artery occlusion is already performed, and that cerebellar atrophy and brain function are improved (non-patent literature 6).

CITATION LIST

Non-Patent Literature

[Non-Patent Literature 1]
J. Chen et al, "Intracerebral transplantation of bone marrow with BDNF after MCAo in rat", Neuropharmacology, 39, (2000) pp. 711-716.

[Non-Patent Literature 2]
O. Y. Bang et al. "Autologous mesenchymalstem cell transplantation in stroke patients", Ann. Neurol., 57, (2005) pp. 874-882.

[Non-Patent Literature 3]
J. Chen et al., "Therapeutic Benefit of Intravenous Administration of Bone Marrow Stromal Cells After Cerebral Ischemiain Rats", Stroke, 32, (2001) pp. 1005-1011.

[Non-Patent Literature 4]
T. Honma et al. "Intravenous infusion of immortalized human mesenchymal stem cells protects against injury in a cerebralischemia model in adult rat", Exp. Neurol., 199, (2006) pp. 56-66.

[Non-Patent Literature 5]
D. Lu et al. "Adult bone marrow stromal cells administered intravenously to rats after traumatic brain injury migrate into brain and improve neurological outcome", Neuroreport, 12, (2001) pp. 559-563.

[Non-Patent Literature 6]
T. Okazaki et al. "Intravenous administration of bone marrow stromal cells increases survivin and Bcl-2protein expression and improves sensorimotor function following ischemia in rats", Neurosci. Lett., 430, (2008) pp. 109-114.

DISCLOSURE OF INVENTION

In order to transplant BMSCs or MSCs intravenously, it is necessary to proliferate the BMSCs or MSCs in vitro in the undifferentiated state. The inventors of the present application have considered that it would be possible to carry graft cells to peripheral veins by blood streams if the size of cultured cells is getting smaller in the proliferation. If graft cells are distributed to peripheral veins, it will improve the survival ratio of the intravenous cell transplantation, and enhance the therapy effect.

Eventually, the inventors have found by trial and error a method of performing in-vitro growth culture of BMSCs or MSCs in the undifferentiated state with the cell sizes reduced.

Therefore, an objective of the present invention is to provide a technique for performing in-vitro growth culture of bone marrow stromal cells (BMSCs) or mesenchymal stem cells (MSCs) in the undifferentiated state with the cell sizes reduced.

In one aspect of the present invention, a culture method of bone marrow stromal cells includes a step of: by culturing bone marrow stromal cells under a pseudo micro-gravity environment generated by multi-axis rotation, obtaining bone marrow stromal cells having an average cell size smaller than that before the culturing.

In one embodiment, said bone marrow stromal cells may be mouse bone marrow stromal cells; in another embodiment, said bone marrow stromal cells may be rat bone marrow stromal cells.

In another aspect of the present invention, a culture method of human mesenchymal stem cells includes a step of: by culturing human mesenchymal stem cells under a pseudo micro-gravity environment generated by multi-axis rotation, obtaining human mesenchymal stem cells having an average cell size smaller than that before the culturing.

In still another aspect of the present invention, a manufacture method of graft cells for a central nerve system diseases therapy includes a step of: by culturing bone marrow stromal cells under a pseudo micro-gravity environment generated by multi-axis rotation, obtaining graft cells which are bone marrow stromal cells having an average cell size smaller than that before the culturing.

The present invention enables performing in-vitro culture of bone marrow stromal cells (BMSCs) or mesenchymal stem cells (MSCs) in the undifferentiated state, while reducing the cell sizes. Also, the present invention enables manufacturing graft cells suitable for a central nerve system diseases therapy.

BRIEF DESCRIPTION OF DRAWINGS

FIG. 2 is a table showing the primer base sequences used for PCR and PCR conditions;

FIG. 17A is a graph showing changes in the cell diameters of cultured cells in a case when human MSCs are cultured; and FIG. 17B is a table showing values of the cell diameters of cultured cells in a case when human MSCs are cultured.

EMBODIMENTS OF INVENTION

In one embodiment of the present invention, bone marrow stromal cells (BMSCs) or mesenchymal stem cells (MSCs) obtained by purification of bone marrow stromal cells are cultured under a pseudo microgravity environment generated by multi-axis rotation. Here, the pseudo microgravity environment means an environment in which the gravity vector integrated over the time is minute as is the case with the space environment.

The pseudo microgravity environment may be generated, for example, by a 3D-clinostat. The 3D-clinostat is an apparatus which provides 360-degree rotation for a sample around two perpendicular axes. The use of a 3D-clinostat enables generating an environment in which the gravity vector integrated over the time is minute (for example, G) as is the case with the space environment.

Figure 1:
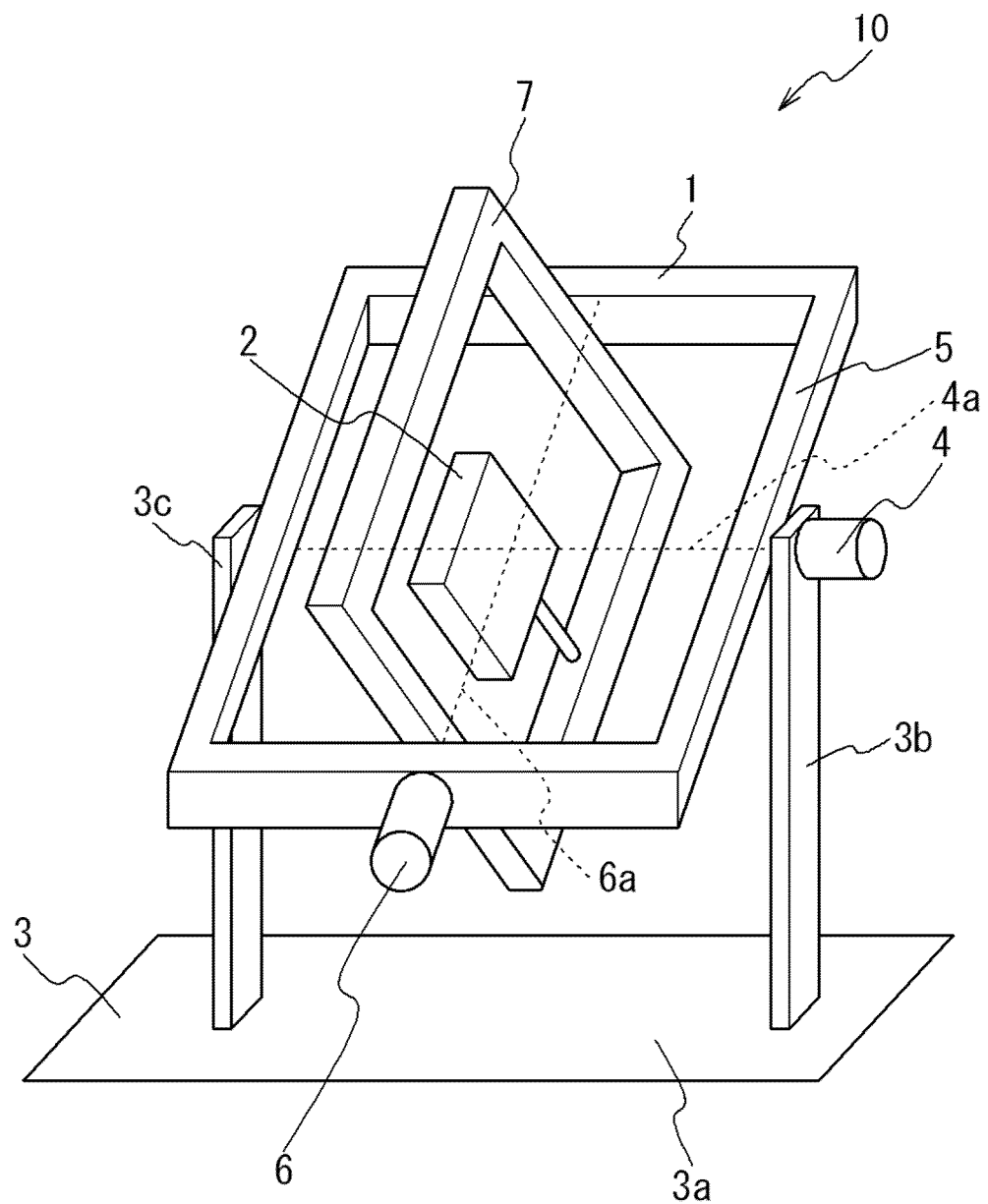
FIG. 1 shows one example of the configuration of a 3D-clinostat in one embodiment of the present invention.

FIG. 1 is a diagram showing one example of the configuration of a 3D-clinostat. The three-dimension clinostat 1 includes a main body 3, a motor 4, an outer frame 5, a motor 6 and an inner frame 7. The main body 3 is disposed on a static system. The main body 3 includes a base portion 3a and legs 3b and 3c. The legs 3b and 3c are coupled to the base portion 3a. The motor 4 is placed on the leg 3b. The motor 4 is coupled to the outer frame 5 and rotates the outer frame 5 about a rotation axis 4a. The motor 6 is disposed on the outer frame 6. The motor 6 is coupled to the inner frame 7 and rotates the inner frame 7 about a rotation axis 6a. The rotation axis 6a is generally orthogonal to the rotation axis 4a. The above-described culture vessel 2 is connected to the inner frame 7. The culture vessel 2 is positioned near the intersection of the rotation axes 4a and 6a. The culture vessel 2 is rotated together with the inner frame 2. The culture vessel 2 is two-axis rotated by the rotations of the outer frame 5 and the inner frame 7. When the culture vessel 2 is two-axis rotated, the gravity applied to cultured cells contained in the culture vessels 2 is dispersed and a pseudo microgravity environment is thereby generated.

A method of culturing BMSCs or MSCs under a pseudo microgravity environment is useful as a manufacture method of graft cells for curing central nerve system diseases. As described later in detail as experimental results, culture of BMSCs and MSCs under a pseudo microgravity environment enables suppressing differentiation of the BMSCs and MSCs. In addition, culture of BMSCs and MSCs under a pseudo microgravity environment enables reducing the cell sizes of the BMSCs and MSCs after the culture. More strictly speaking, culture under a pseudo microgravity environment enables reducing the average size (cell area or cell diameter) of the BMSCs and MSCs after the culture compared to that before the culture. These phenomena improve the survival ratio in a case when BMSCs or MSCs cultured under a pseudo microgravity environment are used as graft cells, enhancing the therapy effect to central nerve system diseases.

In the following, a detailed description is given of examples of the present invention.

Example 1

In example 1, mouse bone marrow stromal cells (mBM-SCs) are cultured under a static environment or a pseudo microgravity environment generated by a 3D-clinostat, and the dynamic state of the mBMSCs under the pseudo microgravity environment was investigated from expression analysis of cell shapes and neural differentiation markers. A 3D-clinostat manufactured by Mitsubishi Heavy Industries, Ltd. was used to generate the pseudo microgravity environment. In addition, mouse brain contusion models are prepared and effects of transplantation of mBMSCs cultured under the pseudo microgravity environment were investigated in view of clinical applications.

1. Experiment Procedure (Culture of Mouse Bone Marrow Stromal Cells)

mBMSCs were obtained from femurs and tibias of C57BL/6 mice at the age of 5-8 weeks. $1.0 \times 10^8$ marrow cells were seeded in culture dishes of a diameter of 90 mm (Thermo Fisher Scientific Nunc A/S brand, Roskilde, Denmark). 48 hours later, floating cells were removed by culture medium exchange, and mBMCSs adhered to the bottom faces of the culture dishes were obtained as cultured cells. Used as growth medium was Dullbecco's modified Eagle's medium (Sigma Aldrich Co.) containing 10% fetal bovine serum (Thermo Fisher Scientific HyClone brand, South Logan, Utah), 100 units/ml penicillin and 100 μg/ml streptomycin (both Sigma-Aldrich Co., Saint Louis, Mo.). It should be noted that mouse marrow cells used for the cell transplantation experiment are similarly obtained from femurs and tibias of GFP transgenic mice (GFP-tg mice) and cultured.

mBMSCs were increased for two passages until the number of cells necessary for the experiment are obtained, and the mBMSCs were seeded in OptiCell™ (Thermo Fisher Scientific Nunc brand, Rochester, N.Y.) at a density of $2.0 \times 10^4$ cells/cm$^2$. The culture was completed when 70% confluent was achieved. The mBMSCs at this timing are referred to as mBMSCs of day 0. The increased mBMSCs were cultured in two different environments, grouped into two groups: a group of the normal 1G environment (group 1G) and a group of the microgravity environment generated by the 3D-clinostat (group CL). Here, each group is further grouped into two groups: a group to be continuously cultured in growth medium and a group to be subjected to differentiation induction by switching to neural induction media. Therefore, the experimental groups consist of group 1G-GM, group CL-GM, group 1G-ND and group CL-ND. The medium for inducing differentiation to nerve cells were prepared by adding 20 ng/ml human fibroblast growth factor basic, 10 ng/ml human β neural growth factor, 10 ng/ml human brain derived neurotrophic factor (all by PeproTech Inc., Rocky Hill, N.J.), B27 supplement (invitrogen Co.), 100 units/ml penicillin and 100 μg/ml streptomycin to Dulbecco's modified Eagle's medium/F-12 (invitrogen Co., Carlsbad, Calif.).

mBMCSs obtained after 7 days of culture (mBMSCs of day 7) were used for observation of the shape changes, analysis by RT-PCR (reverse transcription polymerase chain reaction) and immunostain, and intravenous cell transplantation.

In addition, additional samples were prepared by additional 7 days of culture under the 1G environment after the 7 days of culture (mBMSCs of day 14). It should be noted that the additional 7-day culture was implemented under the 1G environment for all the groups (also for groups CL).

(Shape Observation)

The morphological changes in the cultured mBMCSs were observed by an inverted phase-contrast microscope and pictures of the cultured mBMCSs were taken randomly. The sizes of the cells were measured as follows: Pictures of the mBMSCs which were acquired by a treatment with 0.1% tripsin were randomly taken and captured to a personal computer. 150 cells were randomly selected for each group from the taken pictures, the cell sizes (diameters) were calculated by using image processing software (ImageJ; National Institutes of Health, Bethesda, Md.).

(RT-PCR)

The sampling for RT-PCR was achieved by using ISOGEN (NIPON GENE Co., Ltd., Toyama, Japan), and RNAs were isolated in accordance with the attached protocol. Reverse transcription reactions were performed by using SuperScript™II (invitrogen Co.), and PCR reactions were performed with BD Advantage™ 2 PCR Kits (BD Biosciences Clontech, Palo Alto, Calif.) by using the generated cDNA as the template. Oct-4 was used as the marker of undifferentiated cells and neurofilament heavy chain (NF-H) was used as the differentiation marker of nerve cells. β-actin was used as the internal control gene. The base sequences of the generated primers (all by Sigma-Aldrich Japan K.K., Sigma Genosys, Hokkaido, Japan) and the PCR conditions are as shown in FIG. 2.

(Immunostaining of Neural Differentiation Marker)

mBMSCs were fixed and subjected to immunostaining. A multi-function microscope (BZ-9000; KEYENCE Co., Osaka, Japan) was used for observation. Monoclonal anti-neurofilament 200 and monoclonal anti-MAP2 (both by Sigma-Aldrich Co.) were used as primary antibodies to NF-H and microtuble associated protein 2 (MAP2), and the dilution ratio was adjusted to 1:200. Alexa Flour (registered trademark) 488 goat anti-mouse IgG (H+ L) (invitrogen Co.) was used as the secondary antibody, and the dilution ratio was adjusted to 1:100. 4', 6-diamidine-2-phenylindole dihydrochloride (DAPI; Kirkegaard & Perry Laboratories, Inc., Gaithersburg, Md.) was used for nuclear staining and the dilution ratio was adjusted to 1:100. Images of the stained cells were taken and the images were captured into the personal computer; the positive ratio was calculated by dividing the number of positive cells by the total number of cells for each primary antibody.

(Preparation of Brain Contusion Model Mice and Cell Transplantation)

C57BL/6 mice at the age of eight weeks were used for preparation of recipient mice (brain contusion model mice) and ultracold temperature was used for the preparation of the brain contusion mice. The detailed procedure was as follows: After the scalp was cut open by 15 mm in the direction of the head-tail axis under anesthesia, a metal probe cooled with liquid nitrogen was put four times for 30 seconds at intervals of 30 seconds across the skull against a portion positioned at the intermediate position of the coronal suture and the lambdoid suture and apart by 3.0 mm in the outer left direction of the sagittal suture (that is, the portion of the corticocerebral motor area), and thereby a brain contusion of a diameter of 4.0 mm was formed. The cell transplantation was performed seven days after the contusion of the brain. Specifically, $3.0 \times 10^5$ cultured cells were suspended to PBS (phosphate buffered saline) of 100 μl and injected retro-orbitally for each mouse. The reason why the cell transplantation was performed seven days after the contusion of the brain was to exclude the influence of inflammation which occurred at the just damaged brain cells. The infiltration of inflammatory cells may function as an obstacle against the survival of graft cells. The mice of group C, which is the control group, were injected with PBS of 100 μl. Also, the mice of group S were subjected only to skin incision of the head. In other words, group S is the sham operation group.

(Motor Function Evaluation)

A beam-walking test and a Rotarod test were performed as motor function tests. In the beam-walking test, the mice were caused to walk on the wooden square pole (with a width of 6 mm and a length of 120 mm), and the number of foot-slips of the right hind leg which was paralyzed for 50 steps was recorded. All the mice were trained for three days before the preparation of the brain contusion models, so that the number of foot slips became five or less.

In the Rotarod test, a Rotarod apparatus (KN-75; NATSUME SEISAKUSHO Co., Ltd., Tokyo Japan) was used and the mice were caused to run on a rod which rotated at 20 rpm and the time durations until the mice fell down the rod were measured. All the mice were trained for three days before the preparation of the brain contusion models so that the mice were able to stay on the rod which rotated at 10 rpm for 100 seconds or more.

(Histological Analysis)

28 days after the brain contusion (21 days after the cell transplantation), the mice were fixed by perfusion under anesthesia and the brain tissues were extracted. The brain tissues were embedded with Tissu-Tek (registered trademark)

O.C.T™ Compound (Sakura Finetechnical Co., Ltd., Tokyo, Japan) and flash-frozen with liquid nitrogen. The frozen samples were sliced with a thickness of 10 μm by a cryostat (Leica Microsystems GmbH, Wetzlar, Germany). The sliced brain tissues were subjected to hematoxylin eosin staining (H&E staining) and immunostaining for NF-H and MAP2, which are neural differentiation markers, and glial fibrillary acidic protein (GFAP), which is an astrocyte differentiation marker. As the primary antibody of the immunostaining, monoclonal anti-neurofilament 200 and monoclonal anti-MAP2 (both by Sigma-Aldrich Co.) were used for NF-H and MAP2 with a dilution ratio of 1:200, and mouse monoclonal GFAP (Abcam plc., Cambridge, UK) was used for GFAP with a dilution ratio of 1:200. Alexa Flour (registered trademark) 594 goat anti-mouse IgG (H+ L) (invitrogen Co.) was used as the secondary antibody with a dilution ratio of 1:100. A multi-function microscope (BZ-9000: KEYENCE Co.) was used for observations of the stained brain tissues.

(Immunostaining of Chemokine Receptor)

The immunostaining of a chemokine receptor was achieved by a method similar to the above-described immunostaining of the neural differentiation markers. Anti-CXCR4 (fusin (H-118); Santa Cruz Biotechnology, Inc., Santa Cruz, Calif.) was used as the primary antibody for CXCR4, which is a chemokine receptor, with a dilution ratio of 1:100.

2. Experimental Result (Influence of Pseudo Microgravity Environment on Cell Shape)

Figure 3:
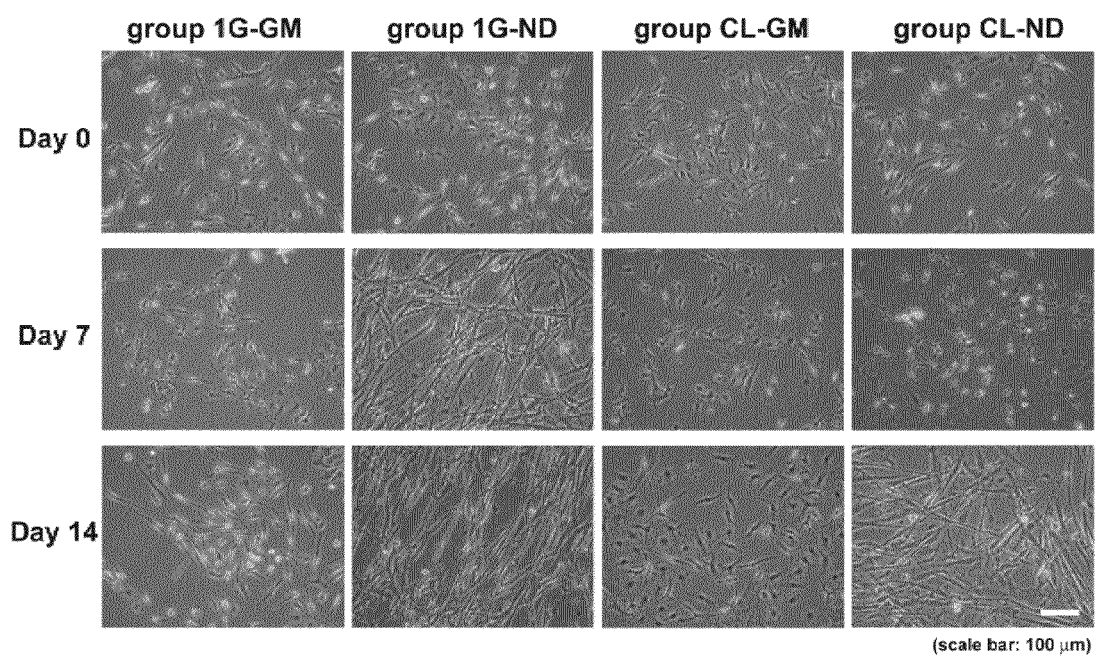
FIG. 3 presents phase-contrast images of mouse BMSCs on day 0, day 7 and day 14.
Figure 4:
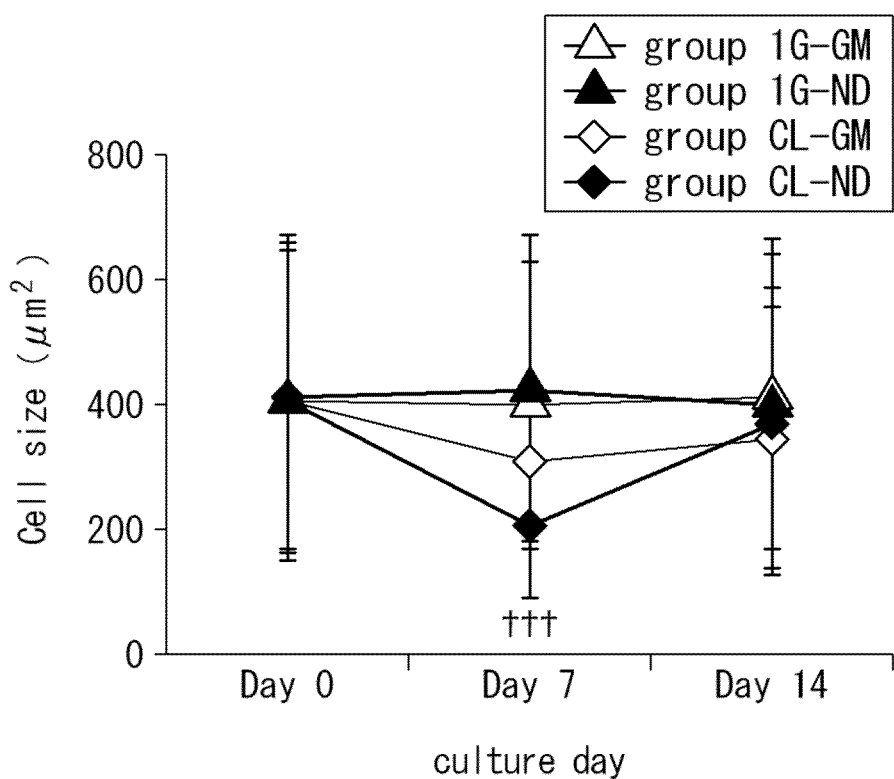
FIG. 4 is a graph showing changes in the cell sizes of cultured mouse BMSCs.

FIG. 3 presents images showing the cell shapes of mBMSCs on day 0 (before the culture), day 7 (after 7 days of culture) and day 14 (after additional 7 days of culture), and FIG. 4 is a graph showing the changes in the cell size caused by such cultures. It should be noted that the additional seven-day culture after the seven-day culture (day 7) was performed under the 1G environment for every group.

As shown in FIG. 3, spindle cells and oval cells were observed before the culture (day 0).

On the other hand, the cell shapes after 7 days of culture (day 7) were as follows: No significant changes were observed in the cell shape for group 1G-GM and group CL-GM, which were groups subjected to the continuous culture in the growth medium. In other words, processes and conjugation of cells caused by differentiation were not observed. For group 1G-ND, which was the group cultured under the 1G environment and subjected to differentiation induction to neuron, on the other hand, a large number of cells were found as protruding long neuroid processes and conjugation of cells was observed. This implies that the cultured cells were differentiated to nerve cells. Under the pseudo microgravity environment, on the contrary, in spite of differentiation induction to neuron, no significant changes were found in the cell shape for group CL-ND, which was the group subjected to differentiation induction to neuron. In other words, no cells protruding long processes were observed for group CL-ND. This suggests a possibility that the differentiation of the mBMSCs to neuron was suppressed under the pseudo microgravity environment.

In order to prove the effect of the culture under the pseudo microgravity environment, after the seven-day culture under the pseudo microgravity environment, additional seven-day culture was performed under 1G-environment (day 14). This resulted in that long neuroid process were found with respect to group CL-ND, as is the case with group 1G-ND (the group cultured under the 1G environment with differentiation induction to verve). In other words, the culture under the 1G environment also caused differentiation for group CL-ND, for which differentiation was suppressed in the culture under the microgravity environment. This result further strongly suggests a possibility that the culture under the pseudo microgravity environment has an effect of suppressing the differentiation of the mBMSCs to neuron.

Furthermore, an effect of reducing the cell size was observed for the groups subjected to the culture under the pseudo microgravity environment (group CL-GM and group CL-ND). FIG. 4 is a graph showing the changes in the cell size of group 1G-GM, group 1G-ND, group CL-GM and group CL-ND, respectively. In FIG. 4, the marks indicate the average values of the cell sizes for each group. For the groups subjected to the seven-day culture under the pseudo microgravity environment (group CL-GM and group CL-ND), the average values of the cell sizes were reduced. This effect was especially apparent with respect to the group subjected to differentiation induction to verve (group CL-ND).

Then, the groups which had been subjected to the seven-day culture under the pseudo microgravity environment (group CL-GM and group CL-ND) were additionally subjected to seven-day culture under the 1G environment; this resulted in that the cell sizes were restored to the original sizes. This suggests further strongly that the culture under the pseudo microgravity environment has an effect of reducing the cell size.

(Influence of Microgravity Environment on Cell Differentiation)

In order to further study the effect on cell differentiation, expressions of an undifferentiation marker and cell differentiation markers were studied. Oct-4 was used as the undifferentiation marker, and neurofilament heavy chain (NF-H) and microtubule associated protein 2 (MAP2) were used as the neural differentiation markers.

Figure 5A:
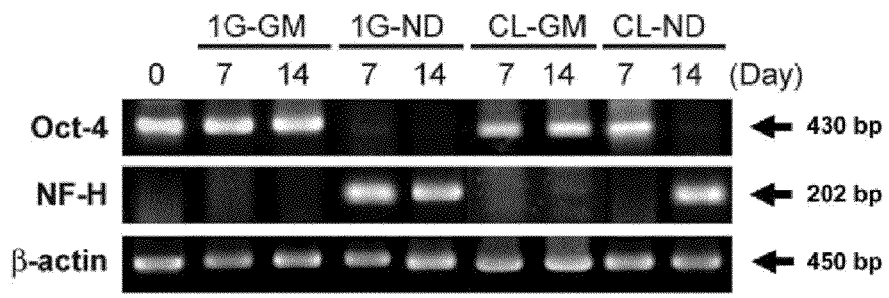
FIG. 5A presents images showing mRNA expressions in mouse BMSCs on day 0, day 7 and day 14.
Figure 5B:
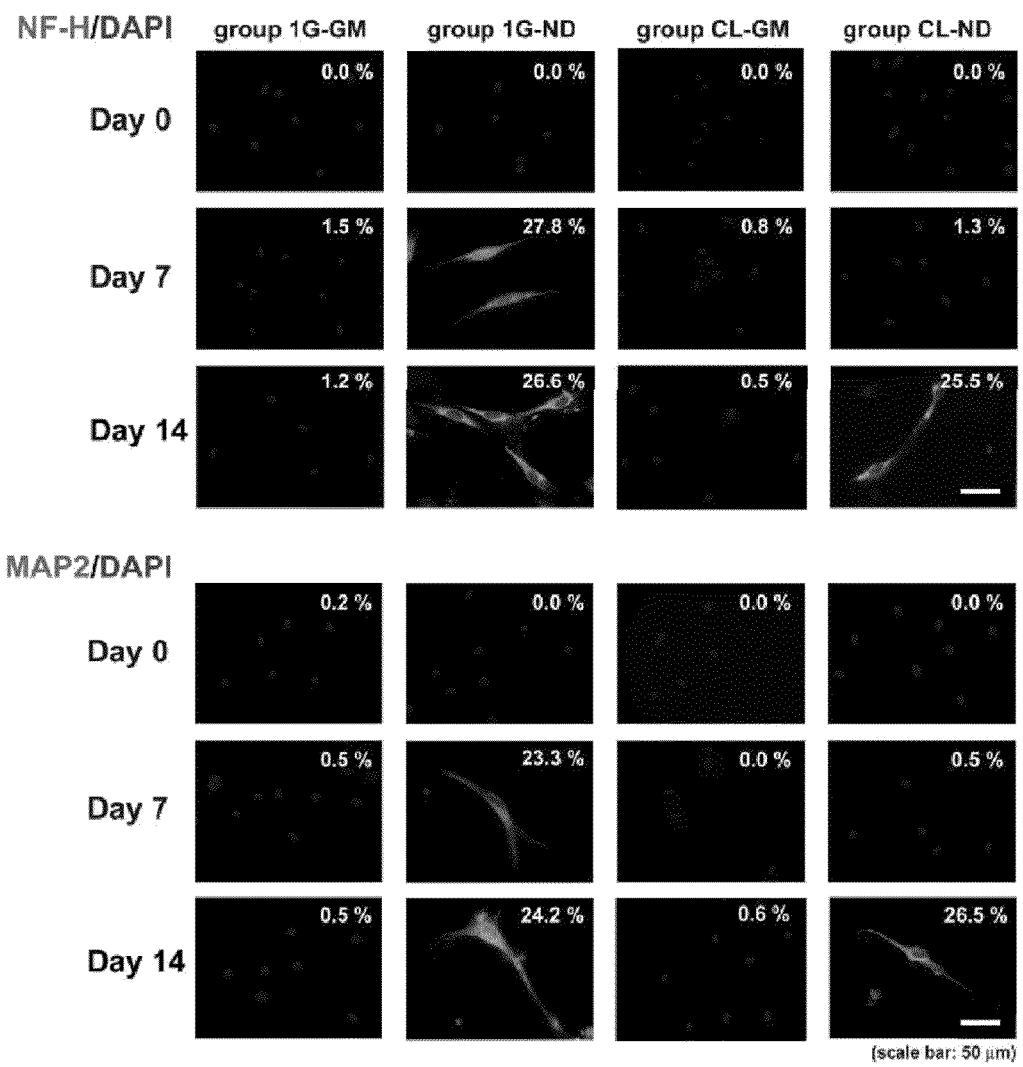
FIG. 5B presents immunostain images of mouse BMSCs on day 0, day 7 and day 14.

FIG. 5A presents images showing mRNA expressions in the respective groups and FIG. 5B presents immunostain images showing protein expressions of NF-H and MAP2 in the respective groups. The numeral values in the respective immunostain images in FIG. 5B form a table indicating the number obtained by dividing the number of cells positive to the detection reaction of the protein expressions of NF-H and MAP2 by the total number of cells.

As shown in FIG. 5A, on day 0, Oct-4 mRNA expressions were observed for the respective groups and no NF-H mRNA expressions were observed.

On day 7, on the other hand, a difference was found in the Oct-4 mRNA expression and the NF-H mRNA expression among the groups. First, for the culture under the 1G environment, a difference was found between the growth medium and the differentiating medium. The details are as follows: for group 1G-GM, the Oct-4 mRNA expression was maintained, while few cells expressed protein NF-H and MAP2, which are neural differential markers. For group 1G-ND, which was subjected to differentiation induction, on the other hand, a weak Oct-4 mRNA expression was observed while NF-H mRNA expression was observed; this confirms that differentiation to neuron occurred for group 1G-ND. Also, as shown in FIG. 5B, protein expressions of NF-H and MAP2 were also observed for group 1G-ND and no difference was found in the positive ratio.

For the culture under the pseudo microgravity environment, on the other hand, no difference was found between the growth medium and the differentiating medium. In other words, for group CL-GM, which was subjected to the culture in the growth medium, an expression of the undifferentiation marker was observed while no expression of the differentiation markers was observed. In addition, for group CL-ND, which was subjected to differentiation induction, an Oct-4 mRNA expression was observed while no expression of the neural differentiation markers was observed Additional seven-day culture was then performed under the 1G environment for all the groups, including group CL-GM (day 14), and this resulted in that, also for group CL-GM, the Oct-4 mRNA expression became weak, while the NF-H mRNA expression became strong as shown in FIG. 5A. Furthermore, as shown in FIG. 5B, protein expressions of NF-H and MAP2 were observed for group CL-ND in addition to group 1G-ND.

This indicates that the culture under the pseudo microgravity environment still suppresses differentiation even when the mBMSCs are subjected to neural differentiation induction, while maintaining undifferentiation states and differentiation ability.

(Motor Function Recovery and Nerve Regeneration by Transplantation)

As discussed above, the culture under the pseudo microgravity environment caused the suppression of the differentiation of the BMSCs and the reduction in the cell size. In the following, a study is presented about effects of motor function recovery and nerve regeneration in a case when mBMSCs cultured under a pseudo microgravity environment are transplanted.

In order to evaluate the in vivo function of the cultured mBMSCs, mouse brain contusion models were generated as central nerve system diseases models and mBMSCs were transplanted to the mouse brain contusion models via veins. The transplantation was performed seven days after the contusion of the brains. A beam-walking test and a Rotarod test were then performed to confirm the effects of motor function recovery and nerve regeneration caused by the transplantation of the mBMSCs. The experimental procedure was as described above. Furthermore, the survival of the graft cells was evaluated by a histological analysis.

Figure 6A:
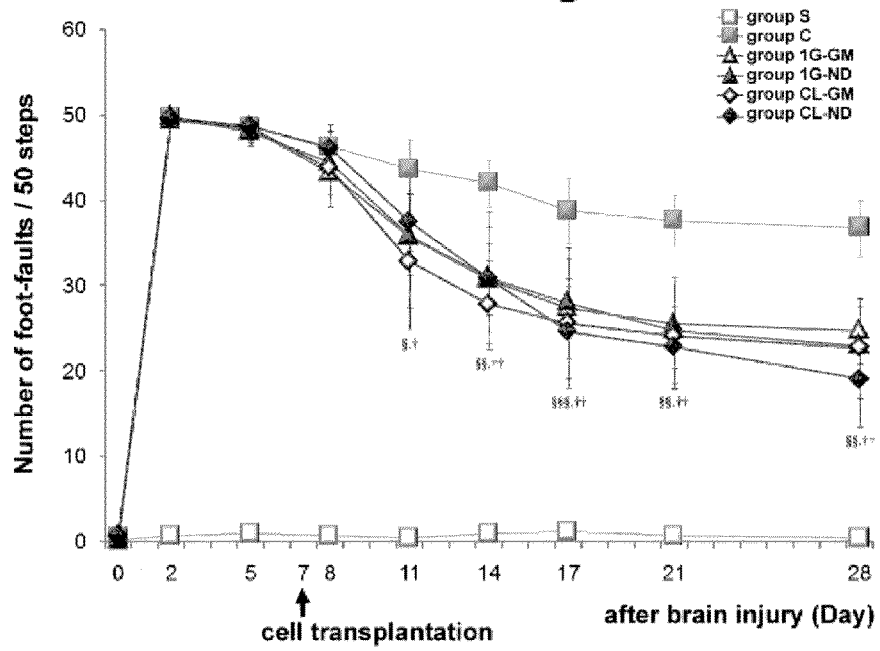
FIG. 6A is a graph showing a result of a beam walking test of mice to which BMSCs are transplanted.

FIG. 6A is a graph showing the result of the beam-walking test. In the beam-walking test, as shown in FIG. 6A, the mice to which the mBMSCs of group CL-ND were transplanted showed significant improvement in the motor function on and after the 11th day from the brain contusion compared to group C, which was only subjected to intravenous injection of PBS, and showed significant improvement on and after the 14th day compared to group 1G-ND, exhibiting motor function recovery most remarkably among the experiment groups. Also, group 1G-GM, group CL-GM and group 1G-ND showed significant improvement on and after the 14th day from the brain contusion compared to group C. Group 1G-ND showed slow recovery, and group CL-GM and group 1G-GM showed recovery at the same level.

Figure 6B:
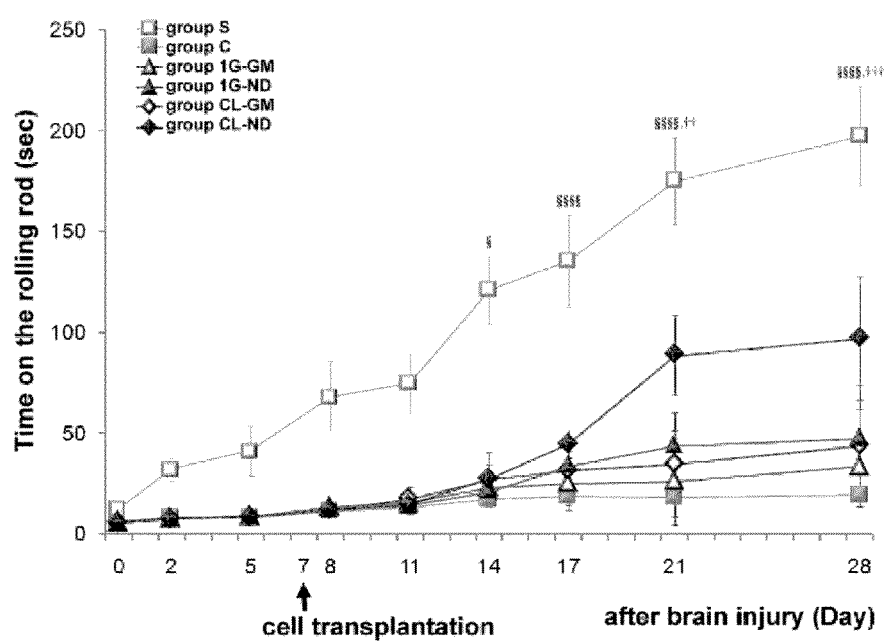
FIG. 6B is a graph showing a result of a rotarod test of mice to which BMSCs are transplanted.

FIG. 6B shows a graph showing the result of the Rotarod test. The same result was obtained in the Rotarod test as the beam-walking test. In detail, the mice to which cells of group CL-ND were transplanted showed significant improvement in the motor function on and after the 14th day from the brain contusion compared to group C, significant improvement on and after the 21th day from the brain contusion compared to group 1G-ND and significant improvement on and after the 28th day from the brain contusion compared to group CL-GM and group 1G-GM.

Figure 7A:
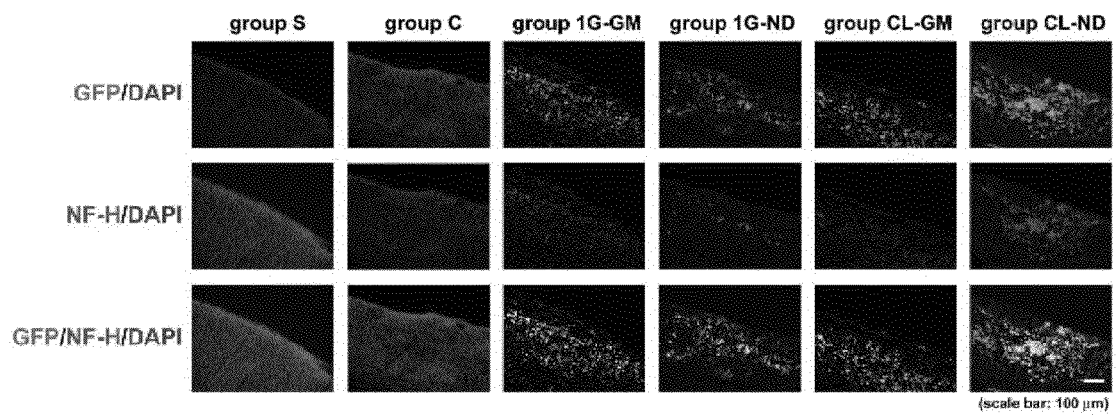
FIG. 7A presents immunostain images of brain tissues stained with NF-H in a case when mouse BMSCs are transplanted.
Figure 7B:
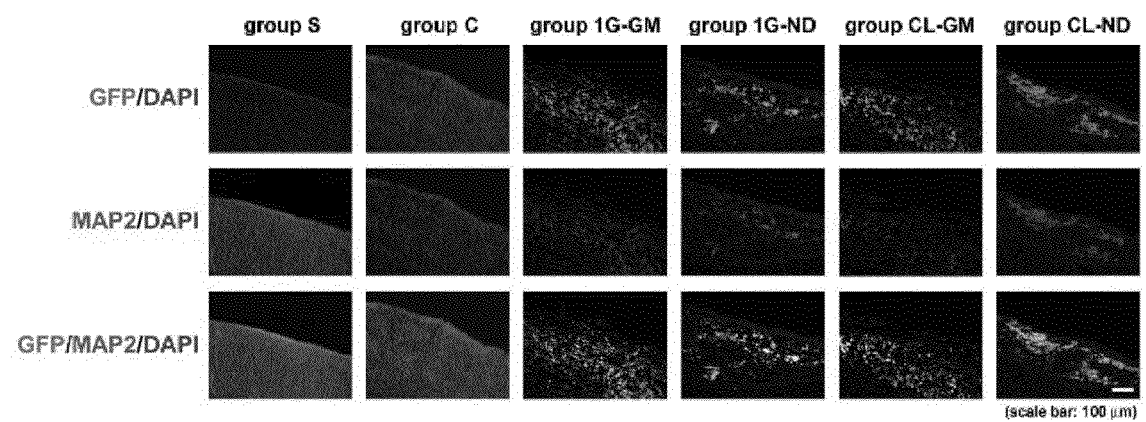
FIG. 7B presents immunostain images of brain tissues stained with MAP2 in a case when mouse BMSCs are transplanted.

FIG. 7A presents tissue images stained with NF-H and FIG. 7B presents tissue images stained with MAP2. For all of group 1G-GM, group CL-GM, group 1G-ND and group CL-ND, graft cells which expressed green fluorescence of GFP were observed at the damaged brain portion 28 days after the brain contusion (21 days after the transplantation). This implies that the mBMSCs transplanted to the mouse brain contusion models had reached the damaged brain portions with respect to the graft cells of all the groups.

Figures 8A, 8B:
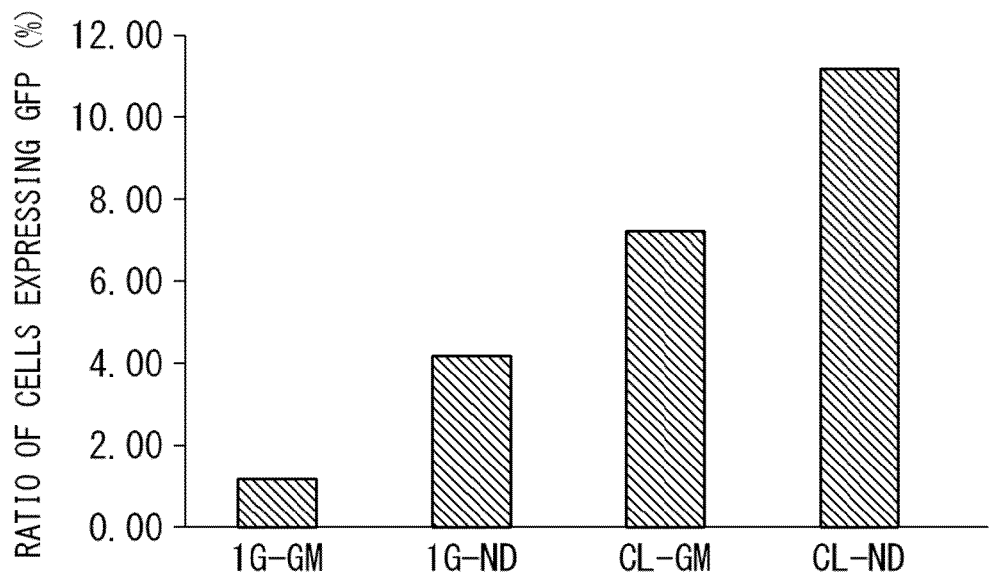
FIG. 8A is a graph showing the existence ratio of graft cells per unit area in a case when mouse BMSCs are transplanted.
FIG. 8B is a table showing the survival ratios and cell sizes of graft cells in brain contusion portions in a case when mouse BMSCs are transplanted.

The area ratios of the GFP positive cells per section were calculated from the tissue images shown in FIGS. 7A and 7B. FIG. 8A is a graph showing the result, and FIG. 8B is a table showing the ratio of the GFP positive cells for each group and the average value of the diameters of the cultured cells for each group. Regarding to the cells cultured under the 1G environment, the area ratios of the GFP positive cells per section were 1.2% for group 1G-GM, and 4.2% for group 1G-ND. Regarding to the cells cultured under the pseudo microgravity environment, on the other hand, the area ratios of the GFP positive cells per section were 7.3% for group CL-GM, and 11.3% for group CL-ND. This result indicates that more graft cells had reached the damaged brain portions in the mice to which cells cultured under the pseudo microgravity environment were transplanted, compared to the mice to which cells cultured under the 1G environment were transplanted (that is, for group CL-GM, compared to group 1G-GM, and for group CL-ND, compared to group 1G-ND). In view of the above-described experimental result of the cell size, the reduction in the cell size can be considered as a factor which causes a larger number of graft cells to reach the damaged brain portions.

Referring back to FIGS. 7A and 7B, expressions of NF-H and MAP2 were observed in some of the graft cells. In the mice to which the cells cultured under the pseudo microgravity environment were transplanted, a larger number of grafts cells which expressed NF-H and MAP2 were observed, compared to the mice to which the cells cultured under the 1G environment were transplanted (that is, for group CL-GM, compared to group 1G-GM, and for group CL-ND, compared to group 1G-ND). Furthermore, a larger number of graft cells which expressed NF-H and MAP2 were observed for group CL-ND, compared to group CL-GM.

(CXCR4 Expression in Graft Cells Cultured Under Pseudo Microgravity Environment)

Although the mechanism of migration of graft cells to a damaged region is not understand, BMSCs subjected to intravenous transplantation are considered as likely to pass through the blood brain barrier in response to a signal or cell surface adhesion factor emitted from the infarct part and to be accumulated at the damaged part. Especially, there has been suggested a possibility that stromal cell derived factor 1 (SDF-1), which shows an increase in the production in the damaged region after the damage, may contribute the selective migration. SDF-1 is one of chemokines which is known as causing lymph cells to migrate in the direction of the concentration gradient, and is coupled to CXCR4, which is one of the CXC type chemokine receptors. Recently, it has been attracting attention that MSCs included in BMSCs express CXCR4 and expression of SDF-1 in the brain contusion region promotes the migration of MSCs injected into a vein. Accordingly, CXCR4 expression of the cultured graft cells was analyzed.

Figure 9:
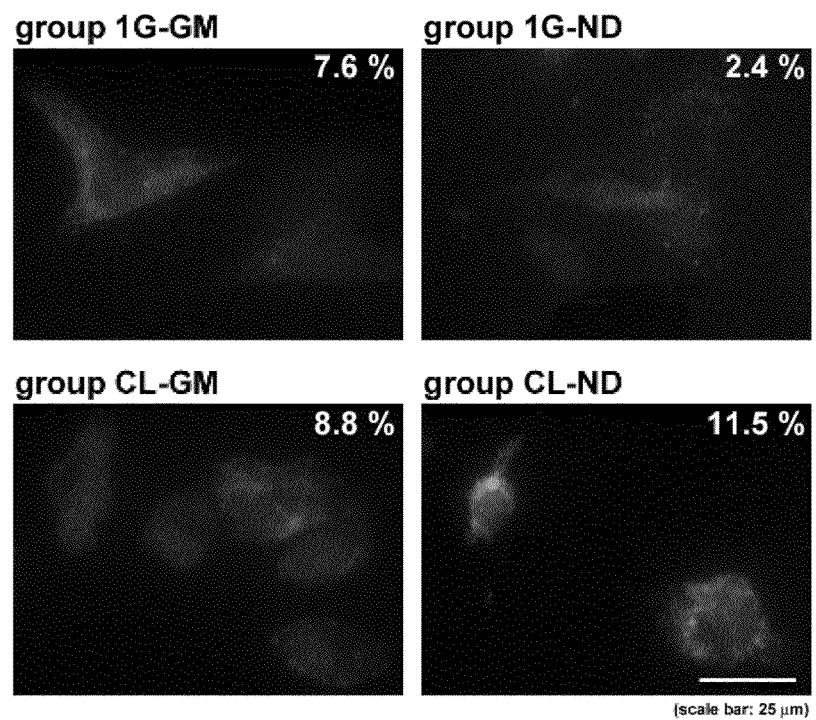
FIG. 9 presents stained images showing CXCR4 expressions of graft cells in a case when mouse BMSCs are transplanted.

FIG. 9 presents cell images obtained by immunostaining of CXCR4. The numeric values in the cell images shown in FIG. 9 indicate the CXCR4 positive ratios of the graft cells. The CXCR4 positive ratios of group 1G-GM and group CL-GM, which were subjected to the culture in the growth medium, were almost same. As for group 1G-ND, which was subjected to the culture in the neural induction medium, only a reduced number of CXCR4-expressing cells were found. As for group CL-ND, a large number of CXCR4-expressing cells were found on the cell membrane and a larger number of positive cells were observed compared to the cells cultured in the growth medium.

The mBMSCs cultured in the growth medium kept the undifferentiating state like MSCs, and included CXCR4-expressing cells; it was therefore considered that the mBMSCs were transported to the damaged brain portion after the transplantation. As for group 1G-ND, which was subjected to differentiation to neuron, only a small number of CXCR4-expressing cells were found and this fact suggests only a small number of graft cells reached the damaged portion. As for the cultured cells of group CL-ND, the result showed that the undifferentiating state are kept against the differentiation induction to neuron, and a large number of CXCR4-expressing cells were found. This is considered as one of the reasons why a larger number of graft cells survived at the damaged portion in the mice to which the cells of group CL-ND were transplanted, improving the motor function.

The above-described experimental results shows that culture under a pseudo microgravity environment, which enables keeping the undifferentiating state and reducing the cell size, is useful as the culture method of graft cells used for a transplantation therapy. Especially, by performing culture under a pseudo microgravity environment with the undifferentiating state kept while inducing differentiation induction, CXCR4-expressing cells can be increased and the motor function can be significantly improved.

Example 2

In example 2, the transplantation effect of bone marrow cells (BMSCs) cultured under a pseudo microgravity environment to spinal cord injury was studied. More specifically, after rat BMSCs were subjected to increasing culture under the static environment (1G environment) or under a pseudo microgravity environment generated by a 3D-clinostat, expression analysis of mRNA and protein of cell migration factor receptors was investigated adaptability as graft cells in a transplantation therapy.

Also, after spinal cord injury model rats were prepared, rat BMSCs cultured under the 1G environment and the pseudo microgravity environment were transplanted thereto via veins and the cell transplantation effect was studied by a histological analysis and a motor function evaluation.

1. Experimental Method

Marrow cells were obtained from femurs and tibias of rats at the acre of five weeks and cultured on culture dishes (Thermo Fisher Scientific Nunc A/S brand) of a diameter of 90 mm. 48 hours later, floating cells were removed by culture medium exchange and cells adhered to the bottom faces of the culture dishes were obtained as cultured cells (rat BMSCs). As growth medium, Dullbecco's modified Eagle's medium (Sigma Aldrich Co.) containing 10% fetal bovine serum (Thermo Fisher Scientific HyClone brand), 100 units/ml penicillin and 100 µg/ml streptomycin (both Sigma-Aldrich Co.) were used. The culture liquid was performed to obtain the number of cells necessary for the experiment. The increased rat BMSCs were seeded in cell culture vessel Opti-Cell™ (Thermo Fisher Scientific Nunc brand). After the seeding, the rat BMSCs were cultured under the 1G environment one day so that the rat BMSCs were adhered to the bottom faces of the culture vessel. The rat BMSCs in this state will be referred to as rat BMSCs of day 0. The experimental groups include a group subjected to culture under the 1G environment (group 1G) and a group subjected to culture under the pseudo microgravity environment (group CL). The cultured cells of both groups were cultured in growth medium.

Spinal cord injury model rats were prepared by forming spinal cord injury in adult female rats of 150 to 200 g at the tenth to eleventh dorsal vertebra levels by a weight drop method. The rat BMSCs of group 1G and group CL cultured in the above-described procedure were transplanted to the spinal cord injury model rats thus prepared. Red fluorescent labels were taken in rat BMSCs to be transplanted by using PKH26 (Sigma-Aldrich Co.) before the transplantation. Immediately after the spinal cord injury, cell suspension including the rat BMSCs were injected into the caudal veins of the rats, and thereby $3.0 \times 10^6$ cells were transplanted per rat. The experimental groups include: rats subjected to intravenous injection of saline immediately after the spinal cord injury (group C), rats to which BMSCs cultured under the 1G environment for seven days were transplanted (group 1G) and rats to which BMSCs cultured under the pseudo microgravity environment for seven days were transplanted (group CL).

The motor function evaluations of the rats were performed before the spinal cord injury (day 0), one to seven days after the spinal cord injury (day 1-7), 14 days after (day 14), and 21 days after (day 21). A Basso-Beatle-Bresnahan locomotor rating scale (BBB score) and an inclined plane method (inclined plane score) were performed as the motor function evaluation. It should be noted that the inclined plane method is a method which involves placing a rat on an angle-changeable plate and measuring the maximum angle at which the rat can maintain the posture.

2. Experimental Result

Figure 10:
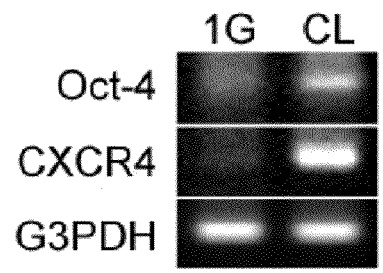
FIG. 10 presents images of mRNA expressions in a case when rat BMSCs are cultured.

FIG. 10 is a diagram showing mRNA expressions of Oct-4 and CXCR4 with respect to group 1G and group CL after the seven-day culture. It should be noted that Oct-4 is an undifferentiated cell marker and CXCR4 is a cell migration factor receptor. The mRNA expression of Oct-4, which is an undifferentiation marker, was observed more strongly for group CL than for group 1G. An expression of mRNA of CXCR4, which is a cell migration factor receptor, was hardly observed for group 1G, while an expression of mRNA of CXCR4 was observed for group CL. Expressions of G3PDH, which is an internal control gene, were the same between group 1G and group CL.

Figure 11:
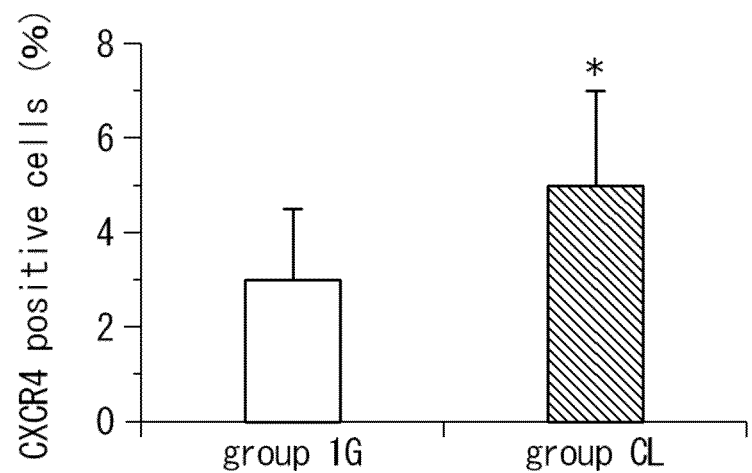
FIG. 11 is a graph showing CXCR4 positive ratios in a case when rat BMSCs are cultured.

FIG. 11 is a graph showing the immunostain positive ratios of CXCR4 for group 1G and group CL after the seven-day culture. The positive ratios were calculated by dividing the numbers of the CXCR4 positive cells, which were obtained from pictures randomly taken for the respective groups, by the total numbers of the cells. As shown in FIG. 11, the results of the immunostain of CXCR4 showed that CXCR4-expressing cells were found for both of the groups. The CXCR positive ratio calculated for group CL was significantly higher than that calculated for group 1G.

Figure 12:
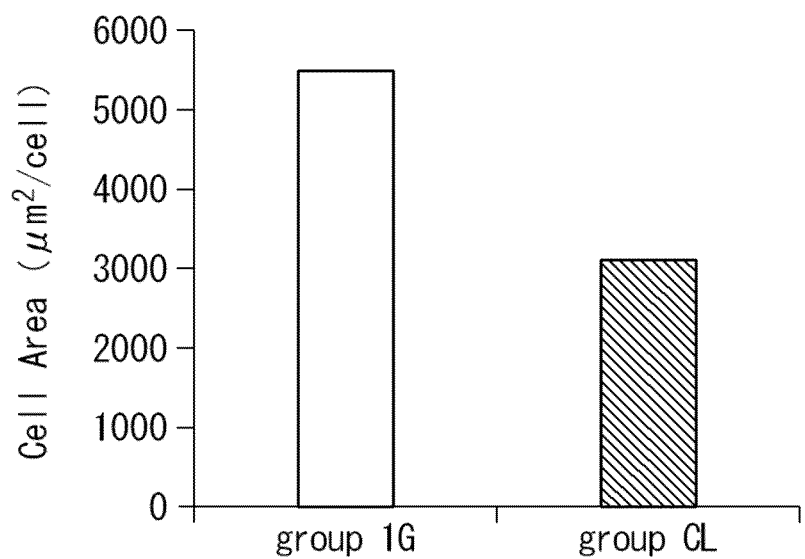
FIG. 12 is a graph showing the cell adhesion areas per cell in a case when rat BMSCs are cultured.

FIG. 12 is a graph showing the sizes of the cultured cells, particularly, the cell adhesion areas per cell. The cell adhesion areas per cell were calculated by dividing the cell adhesion areas by the number of the cells. The cell adhesion area per cell of group CL was smaller than that of group 1G. Also in phase-contrast images, the cells of group CL were observed as smaller than the cells of group 1G.

Figure 13A:
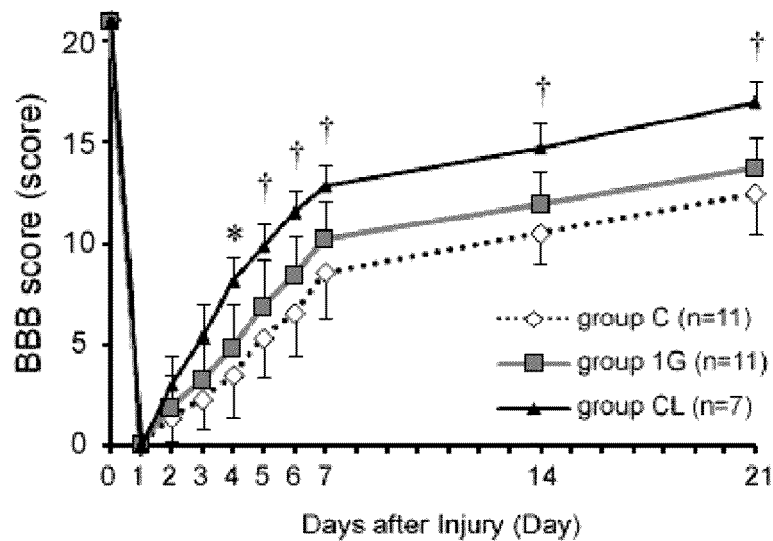
FIG. 13A is a graph showing BBB scores of rats to which BMSCs are transplanted.
Figure 13B:
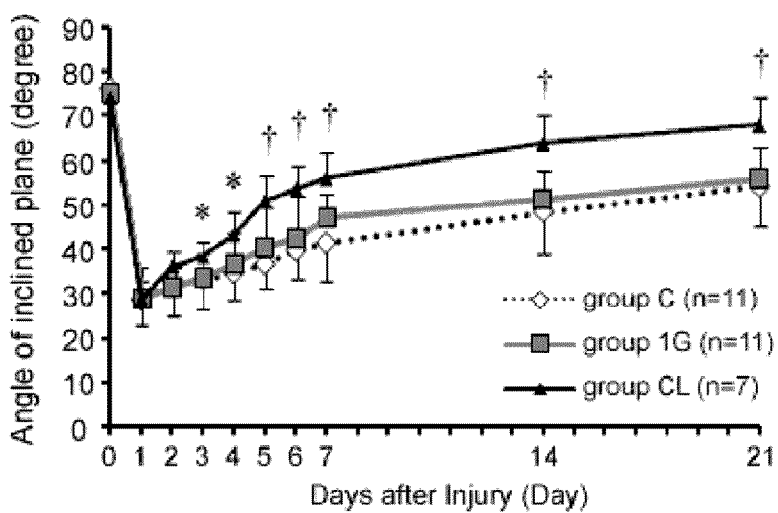
FIG. 13B is a graph showing inclined plane scores of rats to which BMSCs are transplanted.

FIGS. 13A and 13B are diagram showing the result of the motor function evaluation of the rats to which the BMSCs of group 1G and group CL are transplanted. In detail, FIG. 13A is a graph showing the BBB scores of the rats to which the BMSCs of group 1G and group CL were transplanted, and FIG. 13B is a graph showing the inclined plane scores. As shown in FIGS. 13A and 13B, group CL showed significant improvement with respect to both of the BBB score and the inclined plane score on and after the third day from the spinal cord injury, compared to the other two groups (group C and group 1G).

Figure 14:
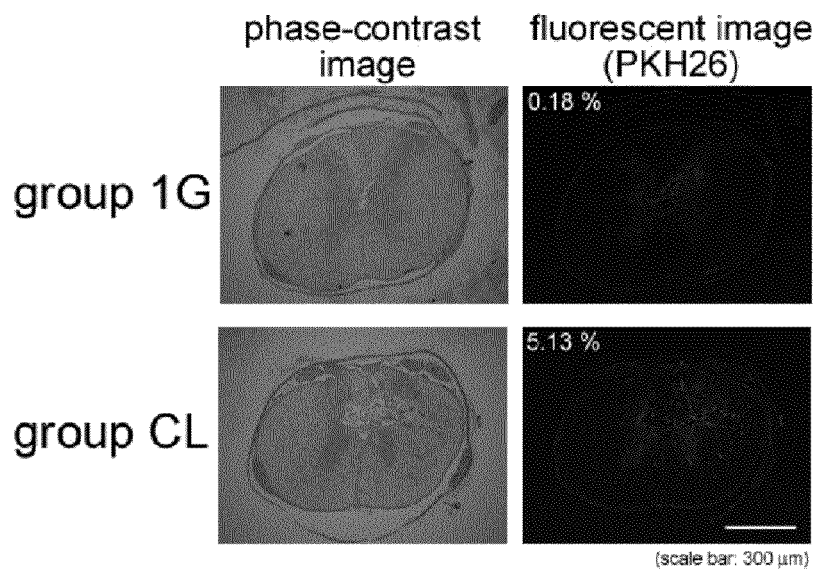
FIG. 14 presents images showing the distributions and existence ratios of graft cells in spinal tissues of rats to which BMSCs are transplanted.

In addition, tissue images of the spinal tissues on the 21th day after the spinal cord injury were observed for both of group 1G and group CL. FIG. 14 presents images showing the graft cell distributions in spinal tissues on the 21th day after the cord injury. The graft cells expressing red fluorescence of PKH26 were observed in the damaged region of the spinal tissues for both of group 1G and group CL. A larger number of graft cells were observed for group CL, compared to group 1G.

Figure 15A:
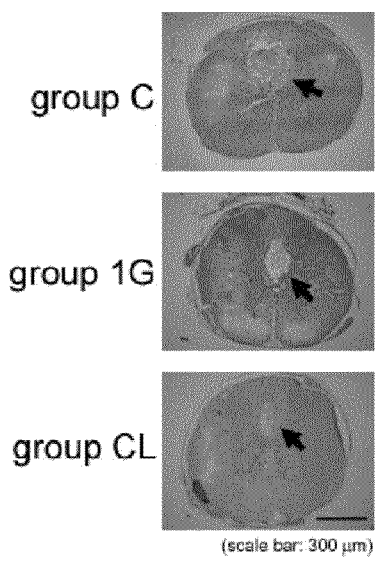
FIG. 15A presents H&E stained images of spinal tissues of rats to which BMSCs are transplanted.
Figures 15B, 16:
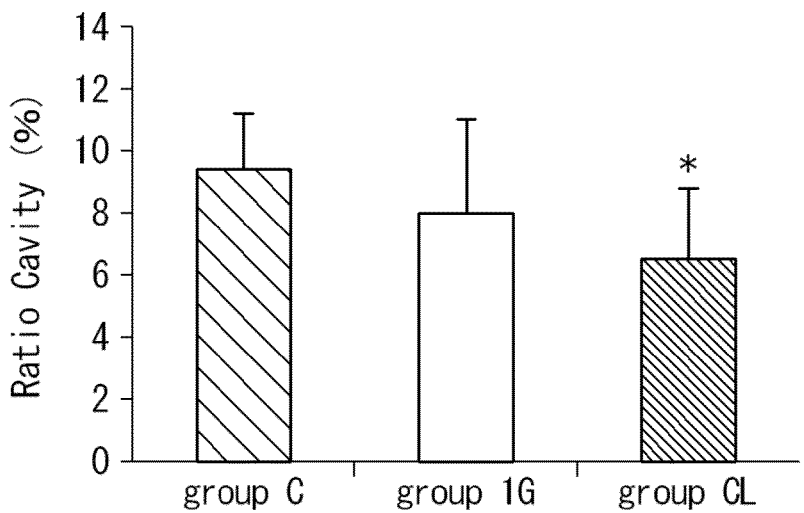
FIG. 15B is a graph showing the cavity percentages in the damaged spinal cord sections of rats to which BMSCs are transplanted.
FIG. 16 is a table showing the relation between the take ratio of graft cells and the culture cell adhesion area in the damaged cord portion.

Furthermore, H&E stain images of the damaged cord portions on the 21th day after the spinal cord injury were observed. FIG. 15A presents H&E stain images of the spinal tissues, and FIG. 15B is a graph showing the cavity percentages. As understood from the H&E stain images on the 21th day after the cord injury, damages between the dorsal funiculus and the center portion and hollowing of the tissues were observed for all of the three groups. As shown in FIG. 15B, the highest cavity percentage of the damaged cord portion was observed on the 21th day after the spinal cord injury for group C; the cavity percentage was significantly reduced for group CL.

As thus described, Oct-4 mRNA expressions were observed after the rat BMSCs were cultured under the pseudo microgravity environment. This suggests that the undifferentiating state of BMCSs is kept by culture under a pseudo microgravity environment. Furthermore, expressions of cell migration factor receptors were increased for group CL.

The graft cells labeled with PKH26 were fixed to the damaged regions of the rat cords 21 days after the intravenous transplantation. As shown in the table of FIG. 16, the graft cell adhesion area for group CL was reduced by 43% compared to group 1G and the survival rate was increased 28 times. An increased number of BMSCs cultured under the pseudo microgravity environment survived in the damaged region, and this significantly reduced the cavity percentage of the damaged portion of the rats subjected to the transplantation, causing significant improvement in the motor function.

The above-described results indicate usefulness of rat BMSCs cultured under a pseudo microgravity environment as graft cells for a central nerve system diseases therapy.

Example 3

In example 3, the effect of culturing human mesenchymal stem cells (hMSCs) under a pseudo microgravity environment was studied. Specifically, human mesenchymal stem cells (Lonza Walkersville, Inc., Walkersville, Md.) were seeded in cell culture vessel OptiCell™ (Thermo Fisher Scientific Nunc brand, Rochester, N.Y.) (day 0), and cultured for seven days under a normal 1G environment or under a pseudo microgravity environment generated by a 3D-clinostat. This means that the experimental groups consists of: a group of hMSCs cultured under the 1G environment (group 1G) and a group of hMSCs cultured under the pseudo microgravity environment.

Growth medium was used for the culture. Dullbecco's modified Eagle's medium (Sigma-Aldrich Co.) containing 10% fetal bovine serum (Thermo Fisher Scientific HyClone brand, South Logan, Utah), 25 units/ml penicillin and 25 μg/ml streptomycin (all by Sigma-Aldrich Co., Saint Louis, Mo.) were used as the growth medium.

FIG. 17A is a graph showing the cell diameters of the cultured cells before and after the seven-day culture, and FIG. 17B is a table showing the specific numerical values of the average cell diameters. After 7 days of culture, the hMSCs cultured under the pseudo microgravity environment (group CL) showed significant reduction in the cell diameter, compared to the hMSCs cultured under the normal 1G environment (group 1G). Furthermore, the hMSCs cultured under the pseudo microgravity environment (group CL) showed significant reduction in the cell diameter after the seven-day culture, compared to that before the culture. Also, it has been confirmed that the culture under the pseudo microgravity environment maintains the undifferentiating state, and the cultured cells are differentiated after the cell transplantation to contribute regeneration of the damaged portion. This indicates superiority of hMSCs cultured under a pseudo microgravity environment as graft cells used in the regeneration medicine.

The invention claimed is:

1. A method of transplanting human mesenchymal stem cells comprising:

culturing human mesenchymal stem cells under a pseudo micro-gravity environment generated by multi-axis rotation, thereby obtaining human mesenchymal stem cells having an average cell size smaller than an average cell size before the culturing; and intravenously transplanting the cultured human mesenchymal stem cells.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
ccgtgaagtt ggagaaggtg                                              20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
tgattggcga tgtgagtgat                                              20

```
<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
agcccaagga ctctacagca                                                  20

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
ctttggcttt tccgtctctg                                                  20

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
gagagggaaa tggtgcgtga                                                  20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
acatctgctg gaaggtggac                                                  20
```